United States Patent
Shrubsole et al.

(10) Patent No.: US 10,405,755 B2
(45) Date of Patent: Sep. 10, 2019

(54) SYSTEM AND METHOD FOR CORE BODY TEMPERATURE MEASUREMENT

(71) Applicant: KONINKLIJKE PHILIPS N.V., Eindhoven (NL)

(72) Inventors: Paul Anthony Shrubsole, Arnhem (NL); Edwin Gerardus Johannus Maria Bongers, Thorn (NL); Hugo Copini, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/291,123

(22) Filed: Oct. 12, 2016

(65) Prior Publication Data

US 2017/0100042 A1 Apr. 13, 2017

(30) Foreign Application Priority Data

Oct. 13, 2015 (EP) .................................. 15189576

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/0008* (2013.01); *A61B 5/4255* (2013.01);
(Continued)

(58) Field of Classification Search
CPC ......... A61B 5/01; A61B 5/015; G01K 13/002
(Continued)

(56) References Cited

U.S. PATENT DOCUMENTS 6,109,784 A * 8/2000 Weiss .................. G01K 7/42
374/164
9,113,774 B2 8/2015 Goto
(Continued)

FOREIGN PATENT DOCUMENTS

DE 102013005900 A1 10/2014
GB 2286684 A 8/1995
(Continued)

OTHER PUBLICATIONS

Kitamura, et al., "Development of a new method for the noninvasive measurement of deep body temperature without a heater", Medical Engineering & Physics, vol. 32, 2010, pp. 1-6.

*Primary Examiner* — Daniel L Cerioni

(57) ABSTRACT

A core body temperature monitoring system comprises a first, core body temperature, thermometer and a second thermometer comprising a heat flux sensor. The second thermometer is for application to the skin for providing temperature monitoring over time. The second thermometer is calibrated using an output from the first core body temperature thermometer during an initial measurement operation. The first thermometer is removably attached to the second thermometer, wherein the first thermometer is adapted for use while attached to the second thermometer, and is then removed when the second thermometer is to be used. This system provides calibration of a flux sensor which is applied to the skin, by using an initial core body temperature measurement. In this way, the functionality and usage of a classic core body temperature thermometer is combined with a wearable continuous monitoring capability.

13 Claims, 2 Drawing Sheets

(51) Int. Cl.
  *G01K 1/14*  (2006.01)
  *G01K 13/00*  (2006.01)
  *G01K 15/00*  (2006.01)
  *G01K 1/16*  (2006.01)

(52) U.S. Cl.
  CPC .......... *A61B 5/6804* (2013.01); *A61B 5/6808* (2013.01); *G01K 1/14* (2013.01); *G01K 1/16* (2013.01); *G01K 13/002* (2013.01); *G01K 15/005* (2013.01); *A61B 2503/04* (2013.01); *A61B 2505/07* (2013.01); *A61B 2560/0214* (2013.01); *A61B 2560/0223* (2013.01); *A61B 2562/0271* (2013.01); *A61B 2562/04* (2013.01)

(58) Field of Classification Search
  USPC ........................................................ 600/549
  See application file for complete search history.

(56) References Cited

U.S. PATENT DOCUMENTS

| | | | |
|---|---|---|---|
| 2005/0245839 A1* | 11/2005 | Stivoric | G06F 19/3418 |
| | | | 600/549 |
| 2006/0056487 A1 | 3/2006 | Kuroda et al. | |
| 2012/0261402 A1* | 10/2012 | Schwerer | H05B 1/0252 |
| | | | 219/494 |
| 2013/0085708 A1 | 4/2013 | Sattler | |

FOREIGN PATENT DOCUMENTS

| | | |
|---|---|---|
| JP | 2007212407 A | 8/2007 |
| JP | 2011133300 A | 7/2011 |
| WO | 2011012386 A1 | 2/2011 |

\* cited by examiner

SYSTEM AND METHOD FOR CORE BODY TEMPERATURE MEASUREMENT

TECHNICAL FIELD

Various embodiments relate to the measurement of core body temperature, in particular but not exclusively using a surface mounted temperature sensor.

BACKGROUND

Core body temperature (CBT) is important as a vital sign in many parts of a hospital as well as in home-monitoring.

Various embodiments may be of interest for home-monitoring applications and specifically for baby monitoring.

When parents are in doubt about their child's health, information seeking is mainly done on the internet, but with limited success. In many cases, the amount of information is overwhelming and creates even more anxiety and uncertainty.

It has been reported that over the last decade, children's emergency department consultations have increased by around 40% and the use of primary care and out-of-hours services has also increased significantly.

Temperature is seen by both parents and GP's as a valuable indicator to determine and track the severity of a sick child and is therefore selected as the main parameter to track. Generally, when parents have doubts if their child is sick, they put their hand on the child's head or neck to determine if the child feels warmer than normal. If the child feels abnormally warm they want to determine if their child might have a fever by measuring the temperature with a rectal or ear thermometer.

In case of febrile symptoms, a study has shown that a third of parents inspect their child's temperature once every 4 hours or more, a quarter of the parents once in 1 to 2 hours and a fifth of the parents inspect their child's temperature once every 30 minutes. The frequency with which the child's core temperature is measured is also influenced by the height of the fever. Although many parents are familiar with the fact that young children can have very high fevers it is still worrisome.

After it has been determined the child has a fever, a temperature monitoring wearable device can be used to keep track of the fever. Especially when parents have to put a febrile child to bed during the night, continuous temperature monitoring can be used to warn parents if the temperature reaches a certain limit or it might be even able to detect febrile convulsions.

Existing home-monitoring wearable products that claim to measure core body temperature continuously on the skin are very inaccurate. There are products on the market available that can continuously track temperature but there are also comfort and reliability issues. Two of the most important requirements are that the wearable should not only be comfortable for the child to wear, it should also be attached and removed from the child in such a manner that it does not add to the discomfort the child is already in.

Commercially available options to measure CBT include invasive rectal probes or approaches involving zero heat flux, which is a method using electronics to create a perfect insulator. Recently, 3M (trade mark) introduced a Spot-On sensor which uses this technique for CBT measurement. Although unobtrusive, the disadvantages of this technique include the requirement of a control loop and heating elements to keep the flow at zero, which makes it a difficult option to integrate in wearable sensing solutions. The 3M product is mainly used inside the hospital rather than at home.

The measurement of CBT using passive sensing of heat flux is also an option and has been previously described, for example in Gunga, Hanns-Christian, et al. "A non-invasive device to continuously determine heat strain in humans." Journal of Thermal Biology 33.5 (2008): 297-307.

The passive sensing relies on measuring the heat flux by using at least two temperature sensors separated by an insulating material. An example of a sensor based on passive sensing is shown in FIG. 1.

The body is shown as layer 10, and the core body temperature to be measured is T0. The sensor comprises an insulating layer 12 with a first temperature sensor 14 against the skin and a second temperature sensor 16 on the opposite side of the insulator layer 12. The temperature sensor at the skin surface measures a temperature T1 and the temperature sensor on the outside measures a temperature T2.

The core body temperature T0 is calculated by:

$$T0 = T1 + \frac{Rbody}{Rsensor} \times (T1 - T2) \qquad \text{Eq. 1}$$

There are two main methods of performing passive CBT measurement; using a single heat flux sensor or a dual heat flux sensor.

The single heat flux approach is the simplest method for performing temperature measurements of remote areas. The single heat flux method requires only two temperature sensors separated by an insulating material as shown in FIG. 1. If the thermal resistivity R of the insulating materials is known, then the heat flow between the two points can be calculated using equation 2:

$$I = \frac{\Delta T}{R} \qquad \text{Eq. 2}$$

The thermal resistivity is given by equation 3:

$$R = \frac{l}{k} \qquad \text{Eq. 3}$$

where l is the distance between the points where temperature is taken and k is the thermal conductivity of the material.

If the layers in FIG. 1 are assumed to be infinitely wide material sheets with constant thicknesses, the thermal flow is only in the perpendicular direction. The same flux flows through both materials and is given by equation 4:

$$I = \frac{T1 - T2}{R1} = \frac{T0 - T1}{R0} \qquad \text{Eq. 4}$$

This can be rewritten as equation 5:

$$T0 = T1 + \frac{(T1 - T2)R0}{R1} \qquad \text{Eq. 5}$$

R1 is the known thermal resistivity of the material used in the sensor. If the body thermal resistivity R0 is known, then this method can be used for measuring T0. However these calculations are only valid for infinitely wide material sheets, since only in these conditions is the heat flow only in the transverse direction. In reality there will also be a lateral component which will cause imperfections in the calculations. A common method is to use a fixed measurement site and estimate the thermal resistivity of the human tissue under the sensor. This might be difficult in practice.

One option is to use a fixed averaged value for the thermal resistivity (R0) of the body. This is one way to deal with the unknown body thermal resistivity, although the value is for each person different. The CBT calculation is directly influenced by the thermal resistivity of the body so that if a fixed thermal resistance of the body is used, the variations of the body resistance will be fully neglected which causes an error in the CBT estimation.

US 2006/0056487 discloses a core temperature monitoring system using two flux sensors, and different characteristics of the two flux sensors enable the unknown heat resistance in the portion from the deep area in the body to the body surface to be cancelled out. It is also suggested that measurements from a known thermometer may also be used by the system. This provides a more complex system with multiple parts and different operations required by the user.

There is therefore a need for an accurate approach to the measurement of core body temperature which is simple for a user.

SUMMARY

According to various embodiments, there is provided a core body temperature monitoring system, comprising:

a first, core body temperature, thermometer;

a second thermometer comprising a heat flux sensor, wherein the heat flux sensor comprises a pad for application to the skin for providing temperature monitoring over time; and a controller for calibrating the second thermometer using an output from the first thermometer during an initial measurement operation, wherein the first thermometer is removably attached to the second thermometer, wherein the first thermometer is adapted for use while attached to the second thermometer, and the second thermometer is adapted for use when detached from the first thermometer.

This system provides calibration of a flux sensor which is applied to the skin, by using an initial core body temperature measurement. In this way, the functionality and usage of a classic core body temperature thermometer (such as a rectal thermometer) is combined with wearable capabilities. The overall system is a single product which requires minimal change to the way a user operates a standard core body thermometer.

The core body temperature enables calibration by allowing a good estimation of the thermal body resistance, which differs from person to person. This resistance can be measured for each person, so by following a specific procedure using the system, variations in this resistance between individuals are compensated. Thus, the controller is for example adapted to determine the thermal resistance of the body and skin (i.e. the thermal path between the core temperature to be measured and the sensor on the skin) and thereby to calibrate the second thermometer.

By arranging the first thermometer to be removably attached to the second thermometer, and using it while attached to the second thermometer, the user has a single device to use. If the core body temperature measurement does not reveal that temperature monitoring (using the second thermometer) is needed, then the system is not used any further, and is cleaned for future use. If the core body temperature measurement reveals that temperature monitoring (using the second thermometer) is appropriate, then the two thermometers are separated and the second is used. The first can then be cleaned for use another time.

The second thermometer may comprise a first temperature sensor for application to the skin and a second temperature sensor spaced from the first temperature sensor by a layer of known thermal resistivity. This provides a single flux sensor. Indeed, only one flux sensor is needed as a result of the calibration procedure.

The first, core body temperature, thermometer may comprise a rectal thermometer.

The connection between the first core body temperature thermometer and the second thermometer may provide a data connection as well as a mechanical connection. Thus, the first, core body temperature, thermometer automatically transmits its data to the second thermometer for calibration purposes.

The second thermometer may comprise a power supply, and the connection between the first thermometer and the second thermometer provides powering of the first thermometer from the power supply. Thus, the overall device has a single power supply.

The second thermometer for example functions as a handle for the use of the first core body temperature thermometer.

The second thermometer may comprise a fixing for mounting and retaining the pad against the skin. In one example the fixing comprises a clip for mounting over a rim of a waist band of an item of clothing or a diaper. It is thus pressed against the skin by the waist band, and it can remain in place for long term monitoring, for example for days or even weeks.

A wireless transmitter may be provided for transmitting the second thermometer readings to a remote device. The remote device may be a mobile phone or other portable device with a suitable app. It can then provide alerts or warnings, even during the night, to the user of the system.

Various embodiments provide a core body temperature monitoring method, comprising:

taking a core temperature measurement using a first, core body temperature, thermometer as an initial measurement operation, wherein the first thermometer is attached to a second thermometer which comprises a heat flux sensor;

detaching the first thermometer from the second thermometer;

applying the second thermometer to the skin;

calibrating the second thermometer using the output from the first thermometer during the initial measurement operation and the measurements made by the second thermometer; and using the second thermometer to provide temperature monitoring over time.

This method provides accurate temperature monitoring using a skin surface sensor, by providing a single initial core body temperature measurement as a calibration.

The thermal resistance of the skin may be determined and used to calibrate the second thermometer. The core body temperature measurement is for example carried out using a rectal thermometer.

The core body temperature measurement is made with the first core body temperature thermometer attached to the second thermometer, then the second thermometer is detached. There is therefore only one device for the user. The second thermometer may be mounted over a rim of a waist band of an item of clothing (e.g. underwear) or a diaper.

BRIEF DESCRIPTION OF THE DRAWINGS

Various example embodiments will now be described in detail with reference to the accompanying drawings, in which.

DETAILED DESCRIPTION

Various embodiments provide a core body temperature monitoring system and method, the system comprising a first, core body temperature, thermometer and a second thermometer comprising a heat flux sensor. The second thermometer is for application to the skin for providing temperature monitoring over time. The second thermometer is calibrated using an output from the first thermometer during an initial measurement operation. The first thermometer is removably attached to the second thermometer, wherein the first thermometer is adapted for use while attached to the second thermometer, and is then detached when the second thermometer is to be used.

This system provides calibration of a flux sensor which is applied to the skin, by using an initial core body temperature measurement. In this way, the functionality and usage of a classic core body temperature thermometer is combined with a wearable continuous monitoring capability.

Figure 1:
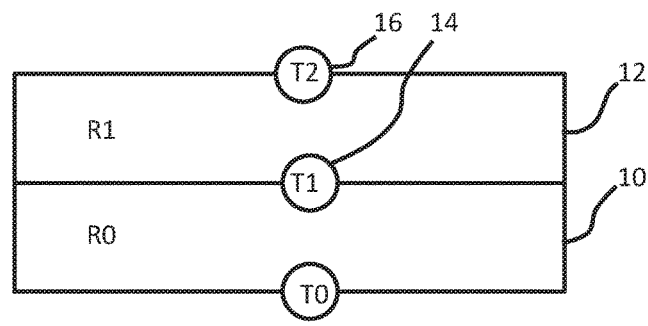
FIG. 1 is used to explain how a single temperature flux sensor functions.
Figure 2:
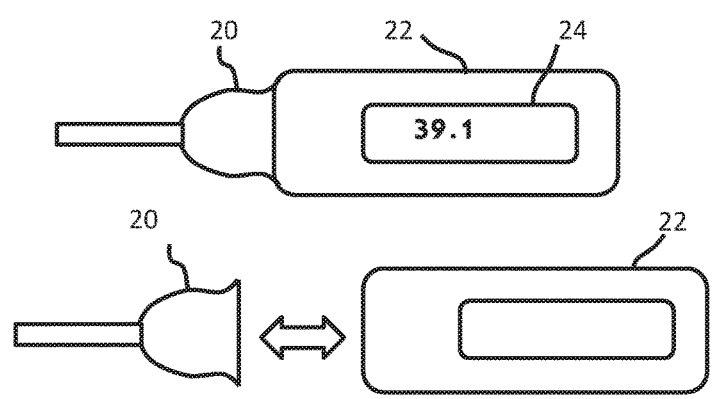
FIG. 2 shows a core body temperature sensor system.

FIG. 2 shows an example of the core body temperature monitoring system.

The system comprises a first, core body temperature, thermometer 20 and a second thermometer 22 which comprises a heat flux sensor.

The first thermometer 20 is removably attached to the second thermometer 22. When the two are attached, as shown in the top part of FIG. 2, the first thermometer 20 is to be used. In this configuration, the second thermometer 22 functions as a handle for the first.

The second thermometer may comprise a display screen 24 for displaying the measurement made by the first thermometer. However, this is entirely optional, as will become apparent from the description below.

The example shows the first thermometer 20 as a rectal thermometer, although it may be an oral or underarm thermometer. It obtains a direct measurement of the inner core body temperature in a known manner, rather than measuring an external skin temperature.

The first thermometer is used for a spot check of the temperature, for example of an infant, and not for continuous monitoring. If the spot check reveals that temperature monitoring may be appropriate, the second thermometer 22 is used for this purpose. The second thermometer comprises a flux sensor of the general type described above, and it is for application to the skin. To use the second thermometer, the first is removed as shown in the lower part of FIG. 2.

The spot check of temperature serves not only as a temperature measurement but also as a calibration step for the second thermometer 22. In particular, with a known core body temperature T0 it becomes possible to calculate the body resistance R0 using Equation 5:

$$T0 = T1 + \frac{(T1 - T2)R0}{R1} \qquad \text{Eq. 5}$$

Thus, the combination of the flux sensor measurements T1 and T2, the known core body temperature T0 and the known thermal resistance R1 of the insulator of the flux sensor itself, enables the body thermal resistance R0 to be derived, and then used to calibrate all future readings from the second thermometer.

The second thermometer has a controller for calibrating the second thermometer using the output from the first thermometer during the initial spot check measurement.

The data collection is entirely automated and requires no user involvement. Instead, each time the first thermometer is used, the measured temperature is stored as the most recent value. For this purpose, the connection between the two thermometers provides a data link between them. The controller is for example mounted in the second thermometer housing.

When the second thermometer is used, the most recent core temperature measurement is used for calibration. The system may detect that the second thermometer is being used based on detecting the disconnection of the two parts, or based on sensing of a temperature in a suitable range by the second thermometer, or by the user activating the second thermometer (i.e. turning it on).

The second thermometer is for application to the skin. It is a flux sensor, for example as described above, and as is well known. It for example comprises a first temperature sensor for application to the skin and a second temperature sensor spaced from the first temperature sensor by a layer of known thermal resistivity. Only one flux sensor is needed.

Figure 3:
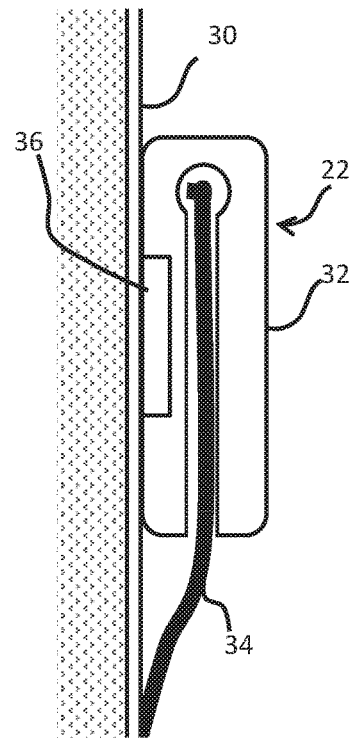
FIG. 3 shows the design of the skin mounted sensor in more detail.

FIG. 3 shows one example of design of the second thermometer 22 which is for mounting over the rim of a waistband of an item of clothing or diaper.

Figure 4:
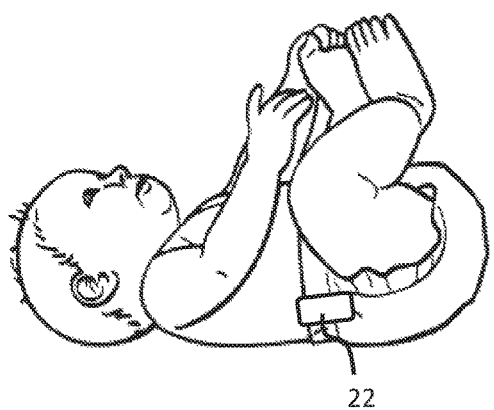
FIG. 4 shows a baby with the skin mounted sensor clipped to a diaper waistband.

FIG. 3 shows the skin of a baby as 30. The second thermometer comprises a housing 32 which clips over the rim of a diaper 34 and so is pressed against the skin. The inner face of the housing carries the flux sensor 36. The mounting of the second thermometer 22 can be seen more generally in FIG. 4.

Of course, the second thermometer may be mounted in other ways, over the chest, waist, or limbs of the subject, either by attachment to clothing, or by attachment to the subject for example by using straps or adhesive patches. Any suitable fixing may be used.

By arranging the first thermometer 20 removably attached to the second thermometer 22, and using it while attached to the second thermometer, the user has a single device to use.

If the spot check does not reveal that temperature monitoring (using the second thermometer) is needed, then the system is not used any further, and is cleaned for future use. If the core body temperature measurement reveals that temperature monitoring (using the second thermometer) is appropriate, then the two thermometers are separated and the second is used. The first can then be cleaned for use another time.

Figure 5:
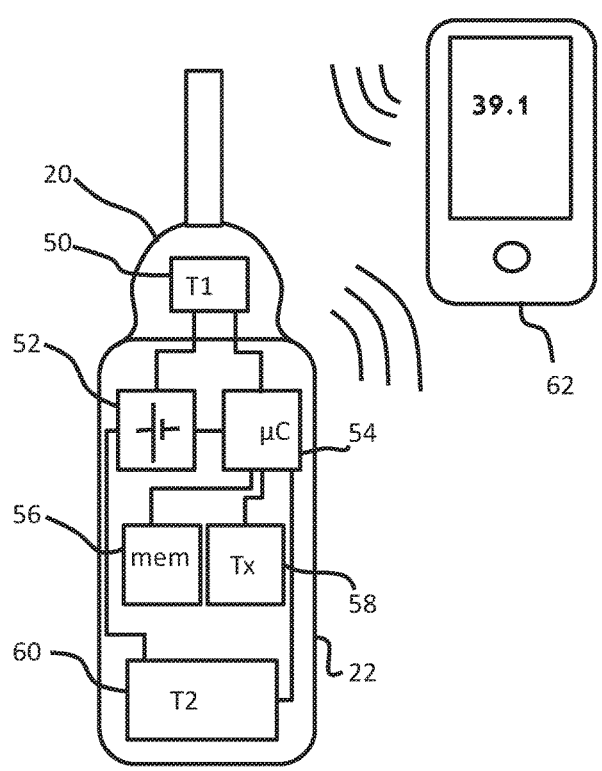
FIG. 5 shows the system of FIG. 2 communicating with a remote device.

FIG. 5 shows one example of the components in the system.

The first thermometer 20 comprises a temperature sensor 50 which is powered by a power source 52 in the second thermometer 22. The connection includes power line connections for this purpose. The output data from the temperature sensor 50 is also provided over a data line to the second thermometer 22. Note that the data connection could be wireless, and the first thermometer could even have its own power supply. In such a case, the connection could be entirely mechanical.

The second thermometer comprises the power source (battery) 52, a controller 54, a memory 56, a wireless transmitter (and optionally also receiver) 58 and the flux temperature sensor 60. The wireless transmitter can use any suitable protocol such as Bluetooth or WiFi.

The memory not only stores the core temperature measurements from the first thermometer 20 but also stores the history of the continuous monitoring temperature data for later communication or for profiling the rate of change of the temperature measurements. This data storage may additionally or alternatively be carried out by a remote device 62 (described below).

The controller performs the calibration function, and any other system functions, such as detection of the connection and disconnection between the two thermometers.

The temperature measurements are sent wirelessly to a remote device 62 such as a smart phone with a suitable app for interpreting and displaying the temperature data. The device 62 can provide alerts or warnings, even during the night, to the user of the system.

The device 62 may also be used for configuring the thermometer, for example to specify how frequently data is provided over the wireless connection (every few minutes or every hour for example).

FIG. 2 shows a display as part of the second thermometer 22. This is optional, in that the remote device may be used. However, for the spot check, an on-board display provides greater ease of use for the user. For the continuous monitoring, a display on a remote device is more convenient.

The system provides a combined core body temperature measurement system having a spot check thermometer (such as a rectal thermometer) and a continuous measurement thermometer. Parents are familiar with the measurement of a baby's rectal temperature, so this initial spot check step is considered to be quite natural for them.

Figure 6:
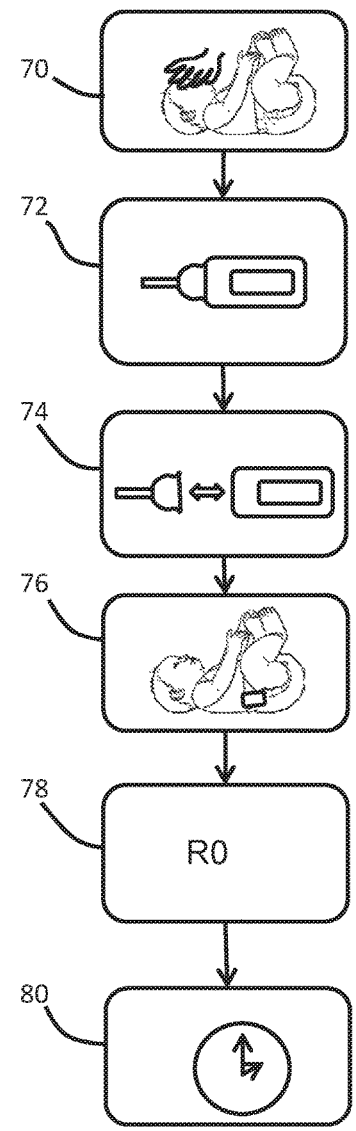
FIG. 6 shows a core body temperature sensing method.

FIG. 6 shows a core body temperature monitoring method. The method is started when a subject (e.g. a baby or infant) shows abnormal behavior.

A user of the system (e.g. a parent of an infant) initially checks the baby by feeling their forehead and neck, in step 70. If the baby feels warmer than usual, the method proceeds to step 72.

In step 72, the user takes a core temperature measurement using the first, core body temperature, thermometer as an initial spot check operation. The temperature measured may be viewed locally on a display screen of the system or on a remote device such as a smart phone.

If the spot check does reveal that the core body temperature is high, the decision is made to provide continuous monitoring.

In step 74, the first thermometer is detached from the second thermometer.

This results in a small wearable hygienic second thermometer. The second thermometer is applied to the skin in step 76, for example by clipping over a diaper or underwear. The flux sensor is applied to the skin.

The system automatically performs a calibration in step 78 using the output from the first thermometer during the initial measurement operation and the measurements made by the second thermometer. This calibration essentially involves calculating the thermal resistance R0 of the body. The flux sensor is then able to provide a reliable estimate of the core temperature.

The second thermometer is used to provide temperature monitoring over time in step 80. The remote device may for example provide an alarm when the temperature reaches a set limit.

Note that the spot check only needs to be carried out once per subject, and is valid during the full subsequent continuous measurement period (which may be up to weeks long).

The processing capability may be in the thermometer arrangement or in the remote device or shared. At one extreme, the thermometer simply sends all raw data to the remote device, and it performs all the calculations and data processing using a remote app. The app controls the whole procedure and makes sure that if the system is used for a different baby or child the thermal body resistivity is determined again.

At the other extreme, all processing is carried out in the thermometer arrangement, and the remote device merely functions as a remote display and alarm system.

The processing may be divided between the local and remote controllers in any manner.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. As used herein, the term "non-transitory machine-readable medium" and similar terms will be understood to encompass both volatile and non-volatile memories, but to exclude transitory signals. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the methods, systems, and principles disclosed herein, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A core body temperature monitoring system, comprising:
   a first, core body temperature, thermometer;
   a second thermometer comprising a heat flux sensor having a known first thermal resistance, wherein the heat flux sensor comprises a pad for application to a wearer's skin for providing temperature monitoring over time; and
   a controller for:
      calculating a second thermal resistance of the wearer's body using the known first thermal resistance and only a single measurement from the first thermometer; and
      calibrating the second thermometer using and the calculated second thermal resistance of the wearer's body and only the single measurement from the first thermometer,
   wherein the first thermometer is removably attached to the second thermometer, wherein the first thermometer is adapted for use while attached to the second thermometer, and the second thermometer is adapted for use when detached from the first thermometer.

2. A system as claimed in claim 1, wherein the second thermometer comprises a first temperature sensor for application to the skin and a second temperature sensor spaced from the first temperature sensor by an insulator layer of known thermal resistivity.

3. A system as claimed in claim 1, wherein the first thermometer comprises a rectal thermometer.

4. A system as claimed in claim 1, wherein the connection between the first thermometer and the second thermometer provides a data connection from the first thermometer to the second thermometer as well as a mechanical connection.

5. A system as claimed in claim 4, wherein the second thermometer comprises a power supply, and wherein the connection between the first thermometer and the second thermometer provides powering of the first thermometer from the power supply.

6. A system as claimed in claim 1, wherein the second thermometer functions as a handle for the use of the first thermometer.

7. A system as claimed in claim 1, wherein the second thermometer comprises a fixing for mounting and retaining the pad against the skin.

8. A system as claimed in claim 1, comprising a wireless transmitter for transmitting output from the second thermometer and optionally output from the first thermometer to a remote device.

9. A core body temperature monitoring method, comprising:
   taking a core temperature measurement of a wearer using a first, core body temperature, thermometer as an initial measurement operation, wherein the first thermometer is attached to a second thermometer which comprises a heat flux sensor having a known first thermal resistance;
   detaching the first thermometer from the second thermometer;
   applying the second thermometer to the wearer's skin;
   calculating a second thermal resistance of the wearer's skin using and the known first thermal resistance and only the core temperature measurement from the initial measurement operation;
   calibrating the second thermometer using the calculated second thermal resistance and of the wearer's skin, the measurements made by the second thermometer, and only the core temperature measurement from the first thermometer during the initial measurement operation; and
   using the second thermometer to provide temperature monitoring over time.

10. A method as claimed in claim 9, wherein the core temperature measurement is carried out using a rectal thermometer.

11. A method as claimed in claim 9, comprising using the second thermometer as a handle for the use of the first thermometer before detaching the first thermometer from the second thermometer.

12. A method as claimed in claim 9, comprising mounting the second thermometer over a rim of a waist band of an item of clothing or a diaper.

13. A method as claimed in claim 9, comprising wirelessly transmitting temperature measurements from the second thermometer to a remote device.

* * * * *